United States Patent
Kirchnavy et al.

[11] Patent Number: 5,728,289
[45] Date of Patent: Mar. 17, 1998

[54] SENSOR CELL HOLDER FOR GAS ANALYZER

[76] Inventors: Steve Kirchnavy; Robert Thompson, both of 1582 Parkway Loop, Suite G, Tustin, Calif. 92680

[21] Appl. No.: 730,673

[22] Filed: Oct. 11, 1996

[51] Int. Cl.⁶ .................................................. G01N 27/26
[52] U.S. Cl. ...................... 205/775; 205/779.5; 205/781; 205/783; 205/784; 205/784.5; 205/785.5; 204/409; 204/415; 204/424; 422/83; 422/104; 422/165
[58] Field of Search ........................... 204/409, 415, 204/424, 279, 286, 287, 297 R; 422/83, 104, 165; 205/775, 779.5, 780.5, 782, 783, 784, 784.5, 785.5, 781

[56] References Cited

U.S. PATENT DOCUMENTS

| | | | |
|---|---|---|---|
| 3,429,796 | 2/1969 | Lauer | 204/195 |
| 4,042,464 | 8/1977 | Blurton et al. | 205/785.5 |
| 4,591,423 | 5/1986 | Murase | 204/428 |
| 4,606,807 | 8/1986 | Mendenhall | 204/409 |
| 5,413,683 | 5/1995 | Murase et al. | 204/183.16 |
| 5,429,737 | 7/1995 | Pribat et al. | 204/426 |
| 5,435,901 | 7/1995 | Friese et al. | 204/429 |
| 5,489,371 | 2/1996 | Joseph et al. | 204/415 |
| 5,538,620 | 7/1996 | Nikolskaja | 205/785.5 |
| 5,582,797 | 12/1996 | Kewley et al. | 204/409 |

*Primary Examiner*—Bruce F. Bell
*Attorney, Agent, or Firm*—John J. Connors; Connors & Assoc.

[57] ABSTRACT

A cell block for housing a sensor cell within a gas analyzer is mounted on the front panel of the analyzer, holding the sensor within a horizontal plane. The cell block is made of inexpensive and non-permeable material such as aluminum which is brazed and anodized. Entry and exit of sample gas is unique as is sample gas exposure to the sensor. Dead space is minimized and response time is improved. An insulated thermister in the cell block maintains accuracy over a wide range of temperatures. The device is RFI and EMI protected.

19 Claims, 4 Drawing Sheets

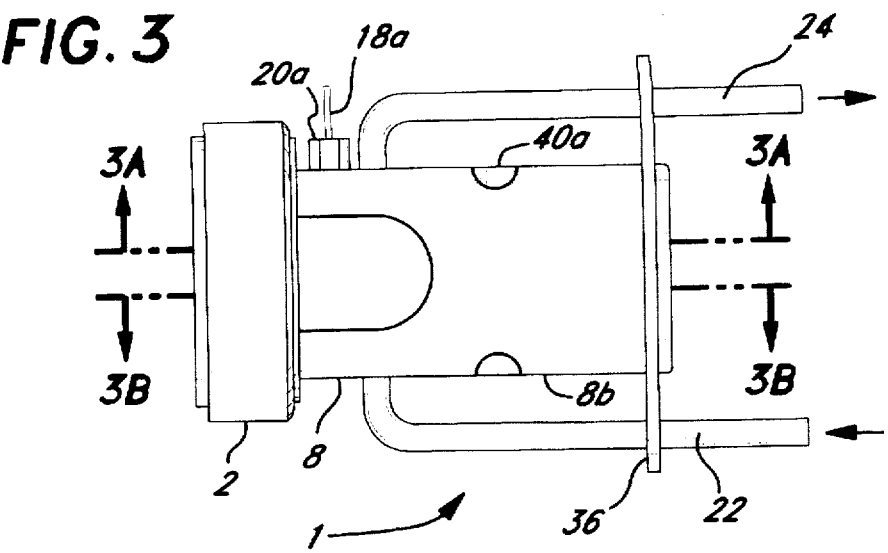
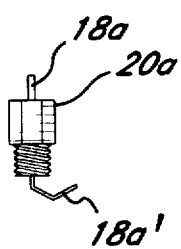
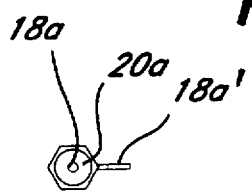
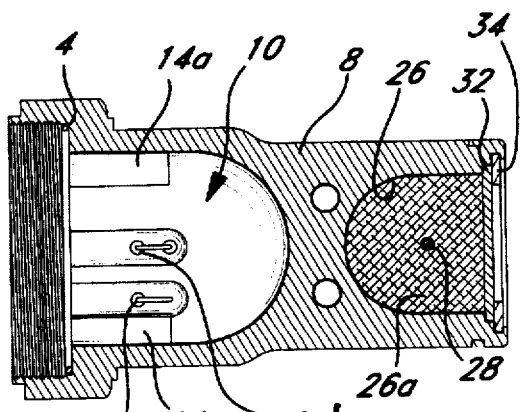
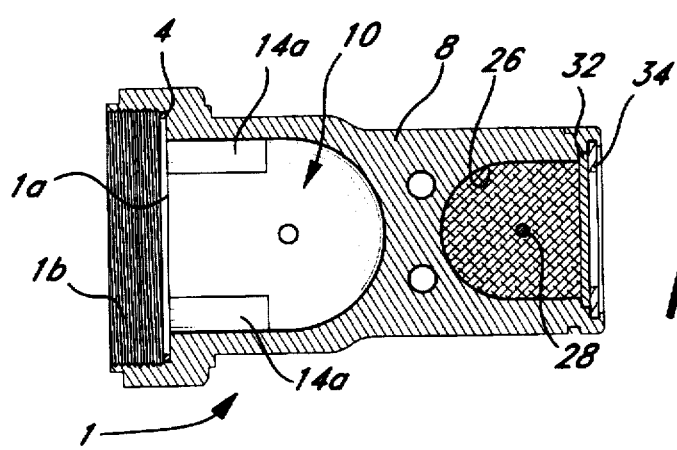

SENSOR CELL HOLDER FOR GAS ANALYZER

BACKGROUND OF THE INVENTION

1. Field of Invention

This invention relates to gas analyzers, and particularly to holder for retaining a sensor cell in a horizontal plane and which is accessed through the front panel of the analyzer and maintains the accuracy of the cell over a wide range of temperatures.

2. Background Discussion

Gas analyzers are commonly available to determine the amount of oxygen or other gases in any sample gas stream both accurately and quickly. These analyzers commonly use some form of sensor cell holder which holds typically an electro-chemical cell sensor. Such holders all suffer from a number of similar disadvantages, namely:

1. The sensor cell holder is either back mounted or internally mounted in difficult to access locations.

2. The sensor cell holder is often mounted in a vertical plane.

3. The sensor cell holder is manufactured of expensive stainless steel or unsuitable semi-permeable material such as nylon.

4. The sensor cell holder chamber has excessive dead space which causes false readings.

5. The sensor cell holder causes the sensor to exhibit slow response times.

6. The sensor cell holder provides inadequate radio frequency interference (RFI) and electro-magnetic interference (EMI) protection for the highly sensitive electro-chemical cell sensors.

SUMMARY OF THE INVENTION

It is the objective of this invention to provide a sensor cell holder for both percent and trace level gaseous oxygen analyzers which eliminates the above cited problems encountered with previous sensor holders. The sensor cell holder of this invention has several key design features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENT," one will understand how the features of this invention provide benefits, which include a a low cost holder which provides front panel access for replacing sensor cells, a unique chamber design to insure elevation of the sensor cell off the floor of the chamber for improved gas circulation within the chamber, and the use of low cost materials which improve the performance of the analyzer.

The first feature of this invention is a sensor cell block having a chamber for receiving the sensor cell. The sensor cell block is modular and is mounted in the gas analyzer so that the chamber is normally disposed horizontally. Preferably, a plurality of mounting holes in the sensor cell block are provided for this purpose, and the sensor cell block is made from a low cost, non-permeable aluminum which is rendered non-corrosive by anodizing the aluminum. A cell block cap removably attached to the sensor cell block seals the chamber. There is inlet and outlet tubing of metal or plastic in communication with the chamber providing ingress and egress for the gas. Preferably, one inlet tube in connected on one side of the chamber and the outlet tube on the opposite side, so that the gas flows around the sensor cell.

The second feature is that the chamber has a floor and an entryway located near a front panel of the analyzer, so that it is simpler and easier to use. Internal walls of the chamber are especially configured to maintain the sensor cell lifted off the floor, so that gas flowing through the chamber circulates freely within the chamber. The chamber is sized so that the cylindrical sensor cell only contacts the internal walls of the chamber at four points. The spacing between the internal walls of the rear portion of the chamber and the surfaces of the cell do not exceed about 0.050 inch to minimize dead space. This provides a superior method for the presentation of gas to the surface of the sensor cell.

The third feature is at least one electrode extending into the chamber to make electrical contact with a sensor cell when said cell is placed in the chamber. The electrode terminates inside the chamber in the form of a spring element that engages the sensor cell upon inserting the cell into the chamber. An insulated feed through located on the sensor cell block insulates the electrode. The feed through has a metal contact wire extending into the chamber to engage a sensor cell placed in said chamber.

The fourth feature is a thermister disposed within a thermister cavity in the sensor cell block. The thermister cavity is filled with an insulating material.

This invention also includes a method of analyzing a gas. This method comprises (a) providing a sensor cell block having a chamber for receiving a sensor cell, (b) passing the gas over the sensor cell with the gas first entering the chamber at an inlet on one side of the sensor cell and then exiting the chamber at an outlet on an other side of the sensor cell, and (c) maintaining the sensor cell within the chamber in condition that enables the gas to flow past essentially all sides of the sensor cell.

DESCRIPTION OF THE DRAWINGS

FIG. 3 is side view of the sample cell holder of the present invention;

FIG. 3A is a cross-sectional view taken along line 3A—3A of FIG. 3;

FIG. 3B is a cross-sectional view taken along line 3B—3B of FIG. 3;

FIG. 8A is a side view of the nylon feed through with contact pin;

FIG. 8B is a plan view of the nylon feed through with contact pin shown in FIG. 8B;

DETAILED DESCRIPTION OF THE PREFERRED EMBODIMENT

Referring to FIGS. 1, 2, 3 and 12, there is shown a sensor cell holder 1 of the present invention mounted in the front panel 90a (FIG. 12) of, for example, an oxygen gas analyzer 3 shown in phantom. Except for the sensor cell holder 1, the oxygen gas analyzer 3 is conventional and includes standard electronic circuitry (not shown) that responds to the electrical output of a sensor cell 6 to provide an electrical signal indicating the amount of, for example, oxygen in the gas being analyzed. A suitable oxygen sensing cell 6 is manufactured by Teledyne Corporation.

Figure 10:
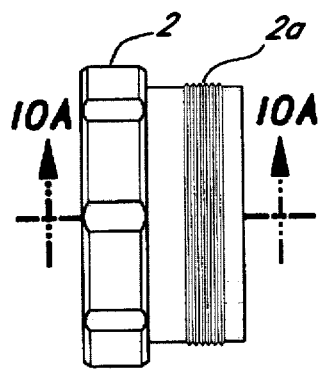
FIG. 10 is the side view of the sensor cell block cap.
Figure 10A:
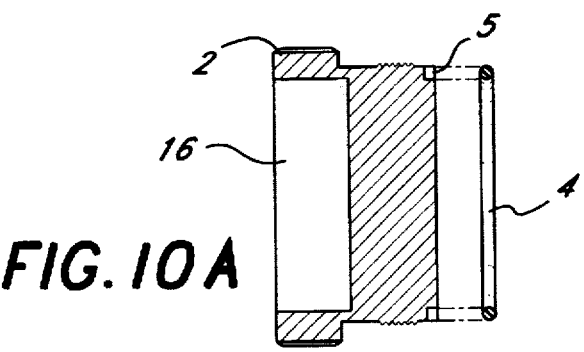
FIG. 10A is the cross-sectional view of the sensor cell block cap taken along line 10A—10A of FIG. 10.

The holder 1 includes a sensor cell block body 8, with an open entryway 1a providing access to an internal chamber 10 in the block body which receives the sensor cell 6. An inlet tube 22 and outlet tube 24 are connected to the block body 8. A sensor cell block cap 2 with threads 2a at the inward end of the cap is screwed into the entryway 1a, which includes internal threads 1b, with an "O" ring 4 serving as a seal to prevent gas from escaping from the chamber 10. The "O" ring 4 is preferably made of a suitable material such as Viton, or other rubber material resistant to corrosive gases. FIG. 10A shows an "O" ring groove 5 machined in the end surface of the cell block cap 2 which seats the "O" ring 4 more securely, thereby, providing a better pressure seal all the way around the "O" ring. The threads of the entryway and cap have a pitch of 32 threads per inch. The fine threads, the "O" ring, and groove 5 provide a gas-tight chamber 10.

Both the sensor cell block body 8 and the sensor cell block cap 2 are made of a suitable material such as aluminum. The preferred method of fabricating both pieces is to use a single piece of round stock of the correct diameter and to machine the necessary chambers and grooves using both a lathe and a mill. The sensor cell block body 8 and the sensor cell block cap 2 are anodized to protect against any corrosive environment within the chamber 10. Since there is a caustic liquid within the sensor cell 6 itself, a puncture in the sensor cell could result in damage to the holder 1. Aluminum was purposely selected as the preferred material. Others have attempted to design sensor cell housings from other materials such as nylon or stainless steel. These materials are undesirable for several reasons. Nylon is no longer acceptable, since nylon permits oxygen to permeate through it reducing accuracy. In addition, the aluminum provides better thermal conductivity for improved heat transfer. Aluminum allows the tubing to be brazed to the body 8. This is highly preferred to epoxy. Stainless steel is extremely expensive (on the order of 10 times more) as opposed to aluminum. Another reason for using aluminum as the preferred material for the sensor cell block body 8 and other components is because it acts as a shield against electromagnetic interference (EMI), RFI (radio frequency interference) or other outside inferences that may otherwise interfere with proper performance of the sensor cell. The combination of the aluminum body 8 brazed with the aluminum tubing also eliminates any thermocouple effects.

Figure 1:
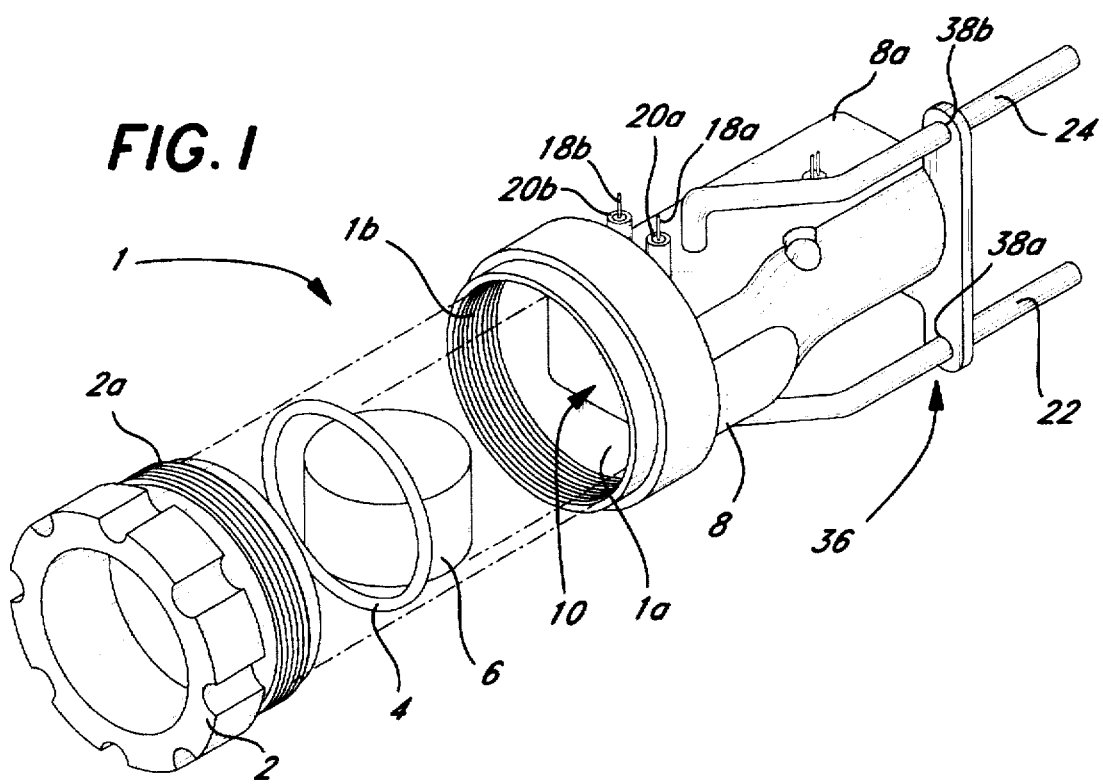
FIG. 1 is an exploded perspective view of the sample cell holder of the present invention.
Figure 9:
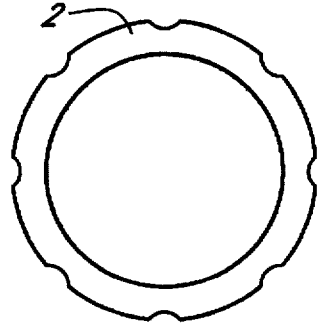
FIG. 9 is the top view of the sensor cell block cap.
Figure 11:
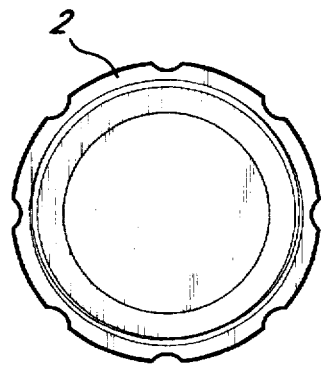
FIG. 11 is the bottom view of the sensor cell block cap.
Figure 7:
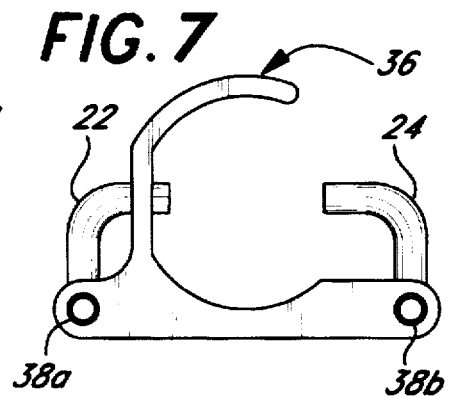
FIG. 7 is a side view of the alignment clip.
Figure 4:
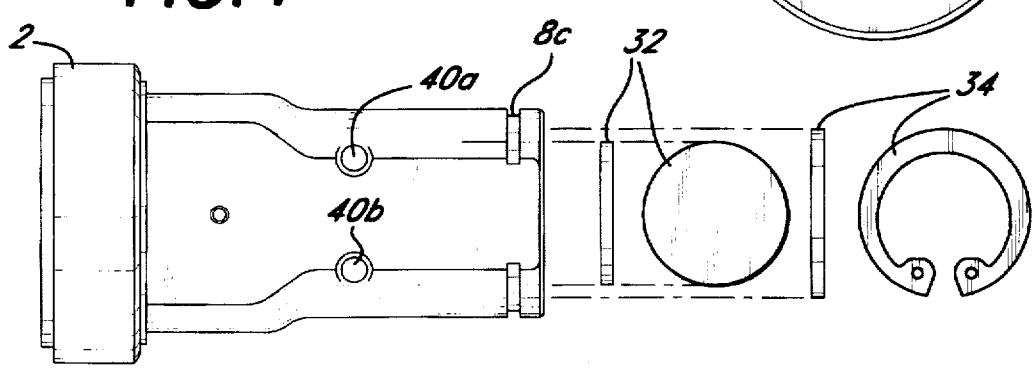
FIG. 4 is the bottom plan view of the sensor cell block body.
Figure 12:
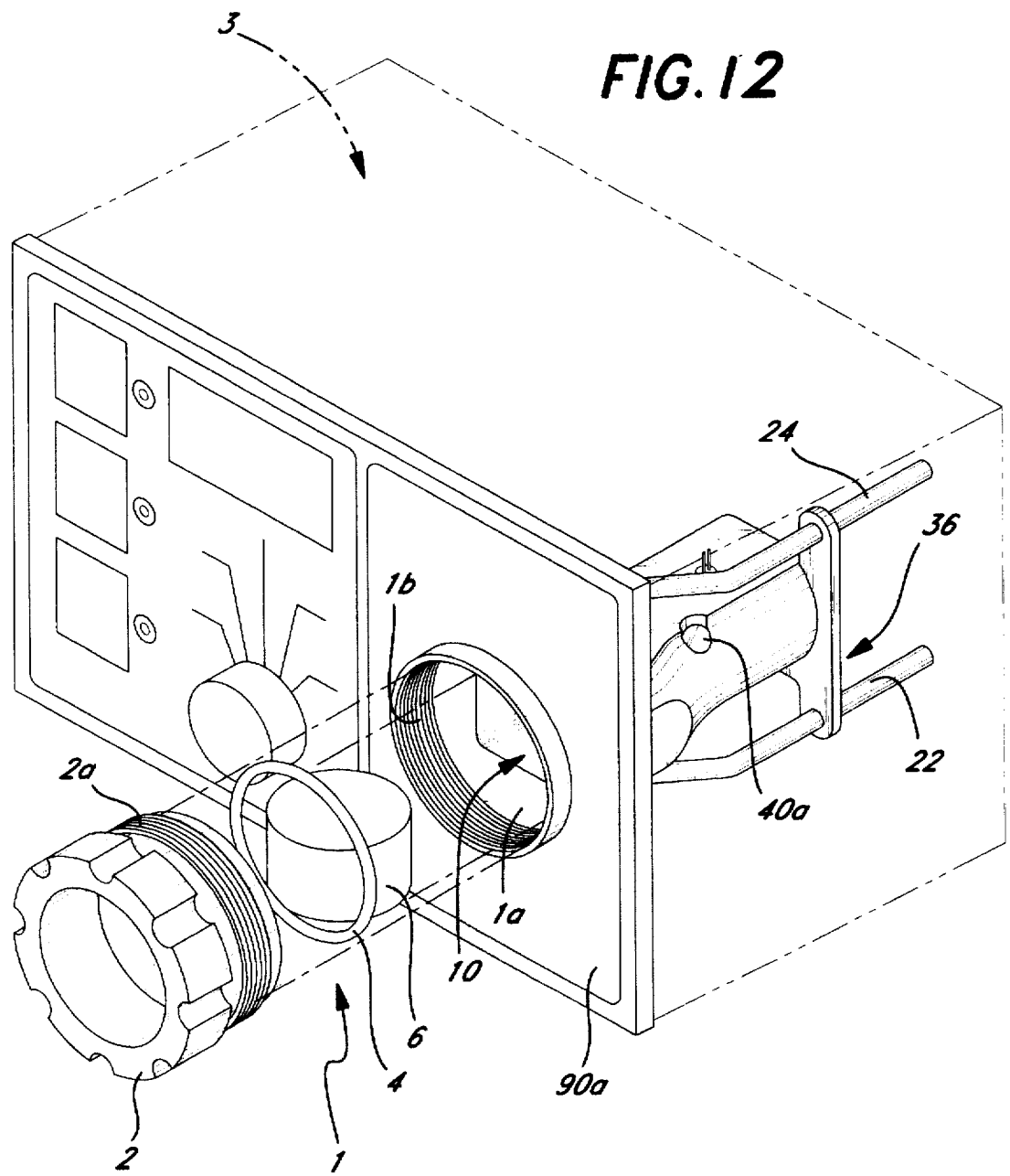
FIG. 12 depicts the front panel with the sensor cell block mounted in place.

An alignment clip 36 shown on FIGS. 1 and 7 is designed to have two holes 38a and 38b for receiving, respectively, the inlet tube 22 and the outlet tube 24. This clip 36 snaps into place in a groove 8c (FIG. 4) in the sensor cell block body 8, securing and stabilizing the inlet and outlet tubes 22 and 24. The alignment clip 36 holds the tubes 22 and 24 in alignment during the brazing process. The alignment clip 36 is brazed into place at the same time as the tubes 22 and 24. When the clip 36 is brazed in place, it is set into a rack and dipped down in a molten flux. The arrangement of the alignment clip 36 solves several problems. It provides support and strength for the aluminum tubes 22 and 24 which are normally weak and could get bent, and it eliminates the need for spot welding prior to brazing.

Figure 5:
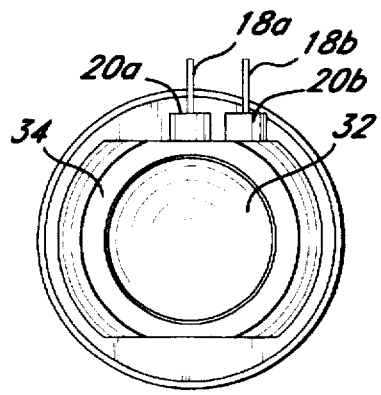
FIG. 5 is the rear view of the sensor cell block body.

As seen in FIG. 3B, machining creates in the sensor cell block body 8 the sensor cell chamber 10 for receiving and holding the sensor cell 6. The sensor cell 6 has a cylindrical configuration. The height of the chamber 10 is slightly greater than the height of the sensor cell 6, and the width of the chamber 10 is slightly greater than the diameter of the sensor cell 6. The curvature in the back surface of the chamber 10 is machined to match the curvature of the sensor cell 5. Consequently, the configuration minimizes much of the dead space within the chamber 10 and improves sensor cell response times. In addition, FIGS. 5 shows a radii 14 machined along all four corners of the sensor cell chamber 10. These radii 14 provide curved sections 14a (FIGS. 3A and 3B) which merge with the top wall and floor of the chamber. When the sensor cell 6 is inserted into the entryway 1a, the curved sections 14a near the floor elevate the cell above the floor, exposing its sensitive surfaces to the sample gas. The spacing of these curved sections is responsible for locating the sensor cell 6 precisely within the chamber 10 to allow gas to flow past the cell. Consequently, the sensor cell 6 makes minimum contact with the internal walls of the chamber 10, allowing gas to flow past the cell. This eliminates the build up of excessive back pressure within the chamber 10. When there is excessive back pressure, the analyzer 3 measures a false high reading when the input gases enter the sensor cell chamber 10. Thus, providing the curved sections 14a eliminates two long standing problems—slow response and false readings.

Figure 2:
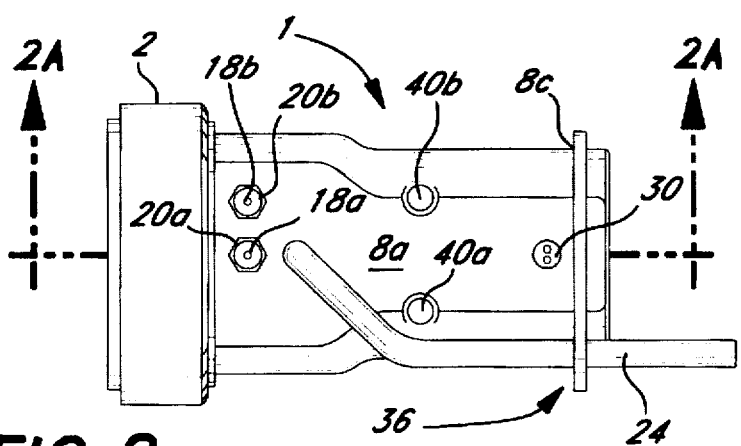
FIG. 2 is a top plan view of the sample cell holder of the present invention.

As shown in FIGS. 1 and 2, electrodes in the form of a pair of spring contact wires 18a and 18b are retained by insulator feed throughs 20a and 20b, preferably made of nylon, which are located on the top of the sensor cell block 8 and are positioned within threaded holes 50 (only one shown in FIG. 2A) that intersect, respectively, with recesses 16a and 16b on the inside wall of the chamber 10. Since the spring contact wires 18a and 18b provide the primary electrical connection with the sensor cell 6, the feed throughs 20a and 20b provide insulation to prevent shorting out the sensor cell to the cell block body 8 as well as providing a seal for the sensor cell chamber 10. In so doing, no outside gases during testing enter the chamber 10, nor oxygen within the sensor cell chamber leak to the outside. This is important since oxygen is being measured at very low concentrations of only a few parts per billion in some instances, for example from 10 to 1,000,000 parts per billion. To further assure a good sensor cell chamber seal, the nylon feed throughs 20a and 20b are sealed with epoxy, and are preferably screwed into the holes 50 with a pitch 32 threads per inch.

Figure 6:
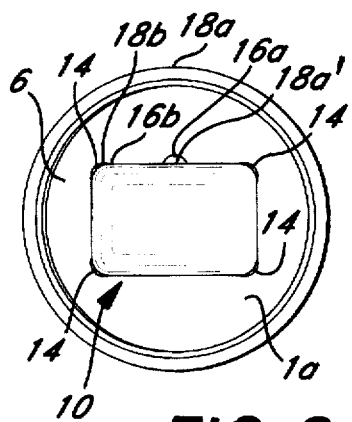
FIG. 6 is a front view of the sensor cell block body with the cap removed and a sensor cell inserted into the chamber.
Figure 2A:
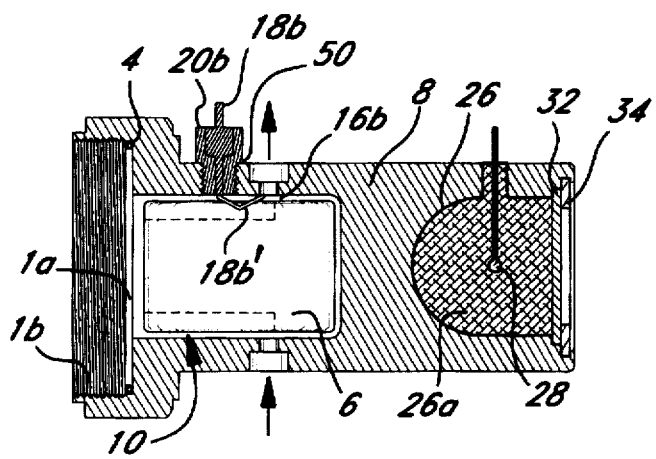
FIG. 2A is a cross-sectional view taken along line 2A—2A of FIG. 2.

As seen in FIGS. 2A, 3A, and 6 there are two recessed areas 16a and 16b machined in the top surface of the chamber 10, one for each of the spring contact wires 18a and 18b. Bent terminal ends 18a' and 18b', respectively, of the spring contact wires 18a and 18b are received in these areas 16a and 16b. The bent terminal ends 18a' and 18b' provide electrical connection with the sensor cell 6 upon engaging the top surface of the Sensor cell 6 when it is inserted into the chamber 10. Without the recesses 16a and 16b, the spring contact wires 18a and 18b could short out to the sensor cell block body 8 when the sensor cell 6 is inserted into the chamber 10 and the spring contact wires 18a and 18b are compressed. In other words, the ends 18a' and 18b' do not contact the inside conductive wall of the chamber 10. The spring contact wires 18a and 18b are made of a suitable material such as gold plated 0.020 music wire or a similar material which is heat treated to retain its necessary springiness. Spring contact wires are used rather than telescopic contacts for two reasons. They do not allow any oxygen to be trapped underneath the sensor cell 6, providing for a quicker recovery time, and they are less expensive to make.

Another important feature of this invention is the way the flow of gas enters and exits the sensor cell block body 8. FIGS. 1 and 3 show the inlet tube 22 is bonded to the bottom 8b of the sensor cell block 8, and the outlet tube 24 bonded to the top 8a of the sensor cell block body 8. These tubes are made of a suitable material such as thick wall ¼" outside diameter (OD) aluminum tubing. The inside diameter (ID) of the tubing is preferably 0.120 and the wall thickness is 0.065. Thick wall tubing is preferred since it eliminates dead volume within the device, but this invention is not a limitation from using other tubing. The tubes 22 and 24 are bonded to the sensor cell block 8 with aluminum dip brazing, thereby creating a perfect seal on both the top and the bottom of the sensor cell block 8 and preserving the overall seal of the sensor cell chamber 10. The use of thick wall tubing and the use of brazing further enhance the improvements of higher sensitivity and faster response.

FIG. 2A depicts a thermister 28 located in the middle of a thermister cavity 26 at the back end 8c of the sensor cell block body 8. The thermister 28 is retained by a threaded nylon feed through 30 (FIG. 2) located on the top 8a of the sensor cell block body 8. Since the thermister resistance varies with temperature in a negative direction, and the output of the sensor cell 6 varies in a positive direction with changes in temperature, the thermister 28 is used to compensate for the change in sensor cell output resulting from changes in temperature. To match the thermal response time of the sensor cell 6 and the thermister 28, it is desired is to slow down the immediate response of the thermister to temperature. This problem has been solved by filling the thermister cavity 26 with a paraffin wax 26a or other suitable insulating material such as, for example, silicon rubber. FIG. 2A shows a disc cover 32 and a snap ring 34 located at the back end 26a of the thermister cavity 26. When the disc cover 32 and snap ring 34 are in place, the thermister and the wax within the thermister cavity 26 are held in place. The disc cover 32 and the snap ring 34 are preferably made of the same material as the sensor cell block body 8, namely, aluminum. Since the purpose of sensor cell 6 is to measure oxygen (not temperature, although that too is possible), a desirable feature of this invention is to compensate the sensor cell for the change in output due to changes in temperature. This is done with an electronic circuit (not shown) including the thermister 28.

A major feature and advantage of the holder 1 of this invention is that it allows front panel mounting on the analyzer 3 and front panel access. FIGS. 3A and 3B show the two mounting holes 40a and 40b used to attach the sensor cell block body 8 to the analyzer. Unique to this invention is immediate horizontal access to the sensor cell 6 without the need to remove analyzer panel 90a as required by other designs. In other designs the block is upside down, or vertical, and within difficult to reach interior space in the analyzer. By using this invention, in a matter of seconds, one simply removes the cap 2 which is on the front of the analyzer panel 90a, replaces the sensor cell 6 in the horizontal plane, and reconnects the cap.

Another advantage of this invention is the manner in which the sample gas enters and exits the sensor chamber 6. The holder 1 allows entry of the sample gas directly from the bottom and exits sample gas directly through the top. This arrangement insures that the flow of gas flows completely around the sensor cell 6 thereby purging the dead spaces very quickly. Because of the metal tubes 22 and 24 provide good thermal conductivity, the gas coming through the tubes 22 and 24 will be brought to the ambient temperature of the analyzer. Any change is going to be seen by the sensor cell 6 more quickly. Because the gas comes in and goes around the entire sensor cell 6, the entire sensor cell is heated uniformly, not just a membrane portion as do others. The gas enters at the bottom, flows through the channels 14a around the sensor cell 6, and exits through the top. This provides a quicker response time, purges any dead space, and allows the gas to surround the sensor cell 6. With other sensor cell holder designs, the gas enters and exits on the same side of the cell, so the gas surrounding the cell is not purged. Consequently, it takes the cell longer to respond and it is not as well temperature stabilized with the holder 1 of this invention.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention:

We claim:

1. A sensor cell holder for a gas analyzer, including a sensor cell block having a chamber for receiving a sensor cell, a cell block cap removably attached to the sensor cell block, said chamber being sealed by said cap, inlet tubing in communication with said chamber, outlet tubing in communication with said chamber, a plurality of insulated feed throughs located on said sensor cell block, each said feed through having a metal contact wire extending into the chamber to engage the sensor cell placed in said chamber, and a thermister disposed within a thermister cavity in said sensor cell block, said thermister cavity being filled with an insulating material.

2. The sensor cell holder of claim 1 including a plurality of mounting holes for mounting said sensor cell block to a gas analyzer.

3. The sensor cell holder of claim 1 where said cap has finely pitched threads.

4. The sensor cell holder of claim 1 where said cap has a groove for receiving an "O" ring.

5. The sensor cell holder of claim 4 where said plastic tubing is affixed to said cell body by a nylon feed through.

6. The sensor cell holder of claim 1 where the tubing is of metal or plastic.

7. The sensor cell holder of claim 1 where the contact wires are of heat-treated gold music wire.

8. The sensor cell holder of claim 1 where the sensor is in a horizontal plane.

9. The sensor cell holder of claim 1 where the sensor cell block is mounted to a front panel of a gas analyzer.

10. The sensor cell holder of claim 9 wherein said thermister cavity is filled with paraffin wax.

11. A gas analyzer, including a sensor cell block having a chamber for receiving a sensor cell, said sensor cell block mounted in the analyzer so that said chamber is normally disposed horizontally with the chamber having an entryway located near a front panel of the analyzer, said chamber having a floor and an internal wall configuration which is adapted to maintain a sensor cell lifted off the floor, so that gas flowing through the chamber circulates freely within the chamber, a cell block cap removably attached to the sensor cell block to cover the entryway and seal said chamber, inlet and outlet tubing in communication with said chamber, and at least one electrode extending into the chamber to make electrical contact with a sensor cell when said cell is placed in the chamber.

12. The analyzer of claim 11 including a thermister disposed within a thermister cavity in said sensor cell block, said thermister cavity being filled with an insulating material.

13. The analyzer of claim 11 where the internal wall configuration has curved sections which merge with the floor, so that the curved sections elevate a sensor cell placed in the chamber off the floor.

14. The analyzer of claim 11 where the electrode terminates inside the chamber in the form of a spring element that engages the sensor cell upon inserting the cell into the chamber.

15. The analyzer of claim 11 where the sensor cell block in made of aluminum.

16. The analyzer of claim 11 where the inlet and outlet tubing are on opposite sides of the sensor cell disposed in the chamber.

17. A method of analyzing a gas comprising (a) providing a sensor cell block having a chamber for receiving a sensor cell, (b) passing the gas over the sensor cell with the gas first entering the chamber at an inlet on one side of the sensor cell and then exiting the chamber at an outlet on an other side of the sensor cell, and (c) maintaining the sensor cell within the chamber in condition that enables the gas to flow past essentially all sides of the sensor cell.

18. The method of claim 17 where the sensor cell is normally disposed horizontally within the chamber.

19. The method of claim 17 where the sensor cell is adapted to detect oxygen.

\* \* \* \* \*